(12) United States Patent
McGall et al.

(10) Patent No.: US 6,833,450 B1
(45) Date of Patent: Dec. 21, 2004

(54) PHOSPHITE ESTER OXIDATION IN NUCLEIC ACID ARRAY PREPARATION

(75) Inventors: Glenn McGall, Mountain View, CA (US); Lisa Kajisa, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/810,434

(22) Filed: Mar. 15, 2001

Related U.S. Application Data (60) Provisional application No. 60/190,167, filed on Mar. 17, 2000.

(51) Int. Cl.$^7$ .......................... C07H 21/00; G01N 33/53
(52) U.S. Cl. .................. 536/25.3; 436/809; 536/25.31; 536/25.32
(58) Field of Search .................. 436/809; 536/23.1, 536/22.1, 25.3, 25.32, 25.31; 435/91.1

(56) References Cited

U.S. PATENT DOCUMENTS

| | | |
|---|---|---|
| 5,143,854 A | 9/1992 | Pirrung et al. |
| 5,242,979 A | 9/1993 | Barnum et al. |
| 5,252,743 A | 10/1993 | Barrett et al. |
| 5,288,514 A | 2/1994 | Ellman |
| 5,324,633 A | 6/1994 | Fodor et al. |
| 5,324,663 A | 6/1994 | Lowe |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,445,934 A | 8/1995 | Fodor et al. |
| 5,451,683 A | 9/1995 | Barrett et al. |
| 5,482,867 A | 1/1996 | Barrett et al. |
| 5,489,678 A | 2/1996 | Fodor et al. |
| 5,491,074 A | 2/1996 | Aldwin et al. |
| 5,510,270 A | 4/1996 | Fodor et al. |
| 5,527,681 A | 6/1996 | Holmes |
| 5,545,531 A | 8/1996 | Rava et al. |
| 5,547,839 A | 8/1996 | Dower et al. |
| 5,550,215 A | 8/1996 | Holmes |
| 5,556,752 A | 9/1996 | Lockhart et al. |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,624,711 A | 4/1997 | Sundberg et al. |
| 5,631,734 A | 5/1997 | Stern et al. |
| 5,658,734 A | 8/1997 | Brock et al. |
| 5,677,195 A | 10/1997 | Winkler et al. |
| 5,710,000 A | 1/1998 | Sapolsky et al. |
| 5,744,101 A | 4/1998 | Fodor et al. |
| 5,744,305 A | 4/1998 | Fodor et al. |
| 5,753,788 A | 5/1998 | Fodor et al. |
| 5,770,456 A | 6/1998 | Holmes |
| 5,800,992 A | 9/1998 | Fodor et al. |
| 5,831,070 A | 11/1998 | Pease et al. |
| 5,843,655 A | 12/1998 | McGall |
| 5,856,011 A | 1/1999 | Sogabe |
| 5,919,523 A | 7/1999 | Sundberg et al. |
| 6,022,963 A | 2/2000 | McGall et al. |
| 6,045,996 A | 4/2000 | Cronin et al. |
| 6,147,205 A * | 11/2000 | McGall et al. |
| 6,300,137 B1 * | 10/2001 | Earhart et al. |

FOREIGN PATENT DOCUMENTS

| | | |
|---|---|---|
| EP | 7288520 | 8/1996 |
| EP | 742287 | 11/1996 |
| EP | 549107 | 12/1997 |
| EP | 967217 A2 | 12/1999 |
| WO | WO 92/10092 | 6/1992 |
| WO | WO 92/10183 | 6/1992 |
| WO | WO 93/04145 | 3/1993 |
| WO | WO 94/10128 | 5/1994 |
| WO | WO 97/10365 | 3/1997 |
| WO | WO 97/27317 | 7/1997 |
| WO | WO 97/39151 | 10/1997 |
| WO | WO 97/43450 | 11/1997 |
| WO | WO 98/20967 | 5/1998 |
| WO | WO 98/39348 | 9/1998 |
| WO | WO 99/00730 | 1/1999 |
| WO | WO 99/40105 | 2/1999 |
| WO | WO 99/54509 | 10/1999 |
| WO | WO 00/06771 | 2/2000 |
| WO | WO 00/21967 | 4/2000 |
| WO | WO 00/61282 | 10/2000 |

OTHER PUBLICATIONS

"Oxidizing Agent Study" (unpublished data); McGall & Kajisa (date?).

McGall et al., "The Efficiency of Light–Directed Synthesis of DNA Arrays on Glass Substrates" *Journal of the American Chemical Society*, 1997, pp. 5081–5090, vol. 119, No. 22.

Lockhart et al., "Expression monitoring by hybridization to high–density oligonucleotide arrays" *Nature Biotechnology*, 1996, pp. 1675–1680, vol. 14.

Saizieu et al., "Bacterial transcript imaging by hybridization of total RNA to oligonucleotide arrays" *Nature Biotechnology*, 1998, pp. 45–48, vol. 16.

Chee et al., "Accessing Genetic Information with High–Density DNA Arrays" *Science*, 1996, pp. 610–614, vol. 274.

(List continued on next page.)

Primary Examiner—Janet L. Epps-Ford
(74) Attorney, Agent, or Firm—Hamilton, Brook, Smith & Reynolds, P.C.

(57) ABSTRACT

Methods are provided for preparing nucleic acid arrays on a support. In these methods a plurality of nucleic acids are synthesized on the support and the synthesis steps include oxidizing a phosphite triester nucleic acid linkage to a phosphate triester nucleic acid linkage using a solution about 0.005 to about 0.05 M iodine in a mixture comprising water and organic solvent.

18 Claims, 2 Drawing Sheets

OTHER PUBLICATIONS

McGall et al., "High–density oligonucleotide probe arrays" Proc. *SPIE–Int. Soc. Opt. Eng.*, 2000, pp. 106–110, vol. 3926 (Advances in Nucleic Acid and Protein Analyses, Manipulation, and Sequencing).

Wallraff et al., "Lithographic techniques for the fabrication of oligonucleotide arrays" *J. Photopolym. Sci. Technol.*, 2000, pp. 551–558, vol. 13.

Glazer et al., "High Surface Area Substrates for DNA Arrays" *Mat. Res. Soc. Symp. Proc.*, 1999, pp. 371–376, vol. 576.

Fidanza et al., "High–Density Nucleoside Analog Probe Arrays for Enhanced Hybridization" *Nucleosides and Nucleotides*, 1999, pp. 1293–1295, vol. 18.

Hacia et al., "Enhanced High Density Oligonucleotide Array Based Sequence Analysis using Modified Nucleotide Triphosphates" *Nucleic Acids Res.*, 1998, pp. 4975–4982, vol. 26.

Pirrung et al., "Proofing of Photolithographic DNA synthesis with 3', 5'–dimethoxybenzoinyloxycarbonyl–protected deoxy–nucleoside phosphoramidites" *J.Org. Chem*, 1998, pp. 241–246, vol. 63.

* cited by examiner

PHOSPHITE ESTER OXIDATION IN NUCLEIC ACID ARRAY PREPARATION

CROSS-REFERENCES TO RELATED APPLICATIONS

This application claims the benefit of 60/190,167, filed Mar. 17, 2000 the disclosure of which is incorporated by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

The present invention relates to improved methods for preparing support-bound nucleic acid arrays. More particularly, the invention relates to methods of preparing the arrays using dilute solutions of iodine to oxidize phosphite ester linkages to phosphate ester linkages.

Substrate-bound nucleic acid arrays, such as the Affymetrix DNA Chip, enable one to test hybridization of a target nucleic acid molecule to many thousands of differently sequenced nucleic acid probes at feature densities greater than about five hundred per 1 $cm^2$. Because hybridization between two nucleic acids is a function of their sequences, analysis of the pattern of hybridization provides information about the sequence of the target molecule. The technology is useful for de novo sequencing and re-sequencing of nucleic acid molecules and also has important diagnostic uses in discriminating genetic variants that may differ in sequence by one or a few nucleotides. For example, substrate-bound nucleic acid arrays are useful for identifying genetic variants of infectious diseases, such as HIV, or genetic diseases, such as cystic fibrosis.

In one version of the substrate-bound nucleic acid array, the target nucleic acid is labeled with a detectable marker, such as a fluorescent molecule. Hybridization between a target and a probe is determined by detecting the fluorescent signal at the various locations on the substrate. The amount of signal is a function of the thermal stability of the hybrids. The thermal stability is, in turn, a function of the sequences of the target-probe pair: AT-rich regions of DNA melt at lower temperatures than GC-rich regions of DNA. This differential in thermal stabilities is the primary determinant of the breadth of DNA melting transitions, even for nucleic acids.

Depending upon the length of the nucleic acid probes, the number of different probes on a substrate, the length of the target nucleic acid, and the degree of hybridization between sequences containing mismatches, among other things, a hybridization assay carried out on a substrate-bound nucleic acid array can generate thousands of data points of different signal strengths that reflect the sequences of the probes to which the target nucleic acid hybridized. This information can require a computer for efficient analysis. The fact of differential fluorescent signal due to differences in thermal stability of hybrids complicates the analysis of hybridization results, especially from combinatorial nucleic acid arrays for de novo sequencing and custom nucleic acid arrays for specific re-sequencing applications. Modifications in custom array designs have contributed to simplifying this problem.

Further complications can arise and lead to variability in diagnostic or sequencing results. For example, degradation of nucleic acid probes, either during the synthesis steps or on standing can lead to variability in assay results. Accordingly, there exists a need for additional methods of nucleic acid array preparation, and the arrays themselves, to provide more robust tools for the skilled researcher. The present invention provides such methods and arrays.

SUMMARY OF THE INVENTION

In one aspect, the present invention provides methods for preparing nucleic acid arrays on a support. In these methods a plurality of nucleic acids are synthesized on the support and the synthesis steps include oxidizing a phosphite triester nucleic acid linkage to a phosphate triester nucleic acid linkage using a solution about 0.005 to about 0.05 M iodine in a mixture of water and organic solvent.

In one group of embodiments, each nucleic acid occupies a separate known region of the support, the synthesizing comprising:

(a) activating a region of the support;

(b) attaching a nucleotide to a first region, the nucleotide having a masked reactive site linked to a protecting group;

(c) repeating steps (a) and (b) on other regions of the support whereby each of the other regions has bound thereto another nucleotide comprising a masked reactive site linked to a protecting group, wherein the other nucleotide may be the same or different from that used in step (b);

(d) removing the protecting group from one of the nucleotides bound to one of the regions of the support to provide a region bearing a nucleotide having an unmasked reactive site;

(e) binding an additional nucleotide to the nucleotide with an unmasked reactive site;

(f) repeating steps (d) and (e) on regions of the support until a desired plurality of nucleic acids is synthesized, each nucleic acid occupying separate known regions of the support;

wherein the attaching and binding steps each form a phosphite triester linkage between the nucleotides and the unmasked reactive sites and further comprise oxidizing the phosphite triester linkage to a phosphate triester linkage with a solution of about 0.005 M to about 0.05 M iodine in an aqueous solvent mixture.

In another group of embodiments, the preparing comprises the sequential steps of.

a) removing a photoremoveable protecting group from at least a first area of a surface of a substrate, the substrate comprising immobilized nucleotides on the J2 surface, and the nucleotides capped with a photoremoveable protective group, without removing a photoremoveable protecting group from at least a second area of the surface;

b) simultaneously contacting the first area and the second area of the surface with a first nucleotide to couple the first nucleotide to the immobilized nucleotides in the first area, and not in the second area, the first nucleotide capped with a photoremoveable protective group;

c) removing a photoremoveable protecting group from at least a part of the first area of the surface and at least a part of the second area;

d) simultaneously contacting the first area and the second area of the surface with a second nucleotide to couple the second nucleotide to the immobilized nucleotides in at least a part of the first area and at least a part of the second area;

e) performing additional removing and nucleotide contacting and coupling steps so that a matrix array of at least 100 nucleic acids having different sequences is formed on the support;

with the proviso that the coupling steps further comprise oxidizing an initially formed phosphite ester to a phosphate ester using an aqueous solution of about 0.005 M to about 0.05 M iodine in an aqueous solvent mixture.

In another group of embodiments, the nucleoside phosphoramidite monomers used in the invention have the formula:

wherein B represents adenine, guanine, thymine, cytosine, uracil or analogs thereof; R is hydrogen, hydroxy, protected hydroxy, halogen or alkoxy; P is a phosphoramidite group; and PG is a photoremoveable protected group.

DETAILED DESCRIPTION OF THE INVENTION

Definitions

The following definitions are set forth to illustrate and define the meaning and scope of the various terms used to describe the invention herein.

"Nucleic acid library" or "array" is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in cornmon with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

"Predefined region" or "preselected region" refers to a localized area on a solid support which is, was, or is intended to be used for formation of a selected molecule and is otherwise referred to herein in the alternative as a "selected" region, a "known" region, or a "known" location. The predefined or known region may have any convenient shape, e.g., circular, rectangular, elliptical, wedge-shaped, etc. For the sake of brevity herein, "predefined regions" are sometimes referred to simply as "regions." In some embodiments, a predefined or known region and, therefore, the area upon which each distinct compound is synthesized is smaller than about 1 $cm^2$ or less than 1 $mrnm^2$. Within these regions, the molecule synthesized therein is preferably synthesized in a substantially pure form. In additional embodiments, a known region can be achieved by physically separating the regions (i.e., beads, resins, gels, etc.) into wells, trays, etc. Accordingly, materials (e.g., nucleic acids) can be synthesized or attached to any particular region by any known methods or means.

General

Nucleic acid arrays having single-stranded nucleic acid probes have become powerful research tools for identifying and sequencing new genes. Other arrays of unimolecular double-stranded DNA have been developed which are useful in a variety of screening assays and diagnostic applications (see, for example, U.S. Pat. No. 5,556,752). Still other arrays have been described in which a ligand or probe (a peptide, for example), is held in a conformationally restricted position by two complementary nucleic acids, at least one of which is attached to a support. Common to each of these types of arrays is the presence of a support-bound nucleic acid and the exquisite sensitivity exhibited by the arrays. Unfortunately, the sensitivity of these arrays can be compromised if the nucleic acids are degraded or are not prepared in sufficient quantity on the support.

In order to provide the reseacher with arrays of uncompromising quality and reproducible performance, arrays should be prepared using high yield reactions and excluding any component which could negatively impact synthesis yield or the performance of the array.

The present invention derives from the discovery that improved yields can be obtained if nucleic acid arrays are prepared using dilute solutions of iodine to oxidize an initially formed phosphite triester linkage to a phosphate triester linkage. Accordingly, the present invention provides methods wherein nucleic acid arrays are prepared using dilute solutions of iodine to effect the desired phosphite/phosphate oxidation.

Embodiments of the Invention

In view of the above discoveries, the present invention provides an improved method of preparing a nucleic acid array on a support. In a general sense, the method comprises synthesizing a plurality of nucleic acids on a support wherein the synthesis steps comprise oxidizing a phosphite ester linkage in a nucleic acid array to a phosphate linkage, by contacting said phosphite ester linkage with a solution of from about 0.005 M to about 0.05 M iodine in water for a period of time sufficient to complete the desired oxidation.

By using dilute solutions of iodine, oxidations which might prove detrimental to other portions of the nucleic acid array are minimized. One of skill in the art will appreciate that the discovery underlying the present invention can be applied to essentially any of the nucleic acid array preparation methods which proceed through a phosphite ester intermediate and require a mild, yet effective oxidation to a phosphate triester.

Synthesis of Nucleic acid Arrays

In the present invention, nucleic acid arrays can be prepared using a variety of synthesis techniques directed to high-density arrays of nucleic acids on solid supports. In brief, the methods can include light-directed methods, flow channel or spotting methods, pin-based methods, bead-based methods or combinations thereof. For light-directed methods, see, for example, U.S. Pat. Nos. 5,143,854, 5,424, 186 and 5,510,270. For techniques using mechanical methods, see PCT No. 92/10183, U.S. Pat. No. 5,384,261 and PCT/US99/00730. For a description of bead based techniques, see PCT US/93/04145, and for pin-based methods, see U.S. Pat. No. 5,288,514. A brief description of these methods is provided below. The methods of the present invention are equally amenable to the preparation of unimolecular double-stranded DNA arrays (see U.S. Pat. No. 5,556,752). In addition, the nucleic acid arrays prepared in the present methods will also include those arrays in which individual nucleic acids are interrupted by non-nucleotide portions (see, for example U.S. Pat. No. 5,556,752 in which probes such as polypeptides are held in a conformationally restricted manner by complementary nucleic acid fragments).

Various additional techniques for large scale polymer synthesis are known. Some examples include the U.S. Pat. Nos. 5,143,854, 5,242,979, 5,252,743, 5,324,663, 5,384, 261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011, all of which are incorporated by reference herein.

Libraries on a Single Substrate

Light-Directed Methods

For those embodiments using a single solid support, the nucleic acids of the present invention can be formed using techniques known to those skilled in the art of polymer synthesis on solid supports. Preferred methods include, for example, "light directed" methods which are one technique in a family of methods known as VLSIPS methods. The light directed methods discussed in U.S. Pat. No. 5,143,854 involve activating known regions of a substrate or solid support and then contacting the substrate with a preselected monomer solution. The known regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of known regions and contacting different monomer solutions with the substrate, a diverse array of nucleic acids is produced on the substrate. Of course, other steps such as washing unreacted monomer solution from the substrate can be used as necessary.

The VLSIP™ methods are preferred for the methods described herein. Additionally, the surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of nucleic acids is produced. Alternatively, an oligomer of from, for example, 4 to 30 nucleotides can be added to each of the known regions rather than synthesize each member in a monomer by monomer approach. Methods for light-directed synthesis of DNA arrays on glass substrates are also described in McGall et al., J Am. Chem. Soc., 119:5081–5090 (1997).

For the above light-directed methods wherein photolabile protecting groups and photolithography are used to create spatially addressable parallel chemical synthesis of a nucleic acid array (see also U.S. Pat. No. 5,527,681), computer tools may be used to assist in forming the arrays. For example, a computer system may be used to select nucleic acid or other polymer probes on the substrate, and design the layout of the array as described in, for example, U.S. Pat. No. 5,571,639.

Flow Channel or Spotting Methods

Additional methods applicable to library synthesis on a single substrate are described in U.S. Pat. No. 5,384,261 and in PCT/US99/00730. In the methods disclosed in this patent and PCT publication, reagents are delivered to the substrate by either (I) flowing within a channel defined on knowvn regions or (2) "spotting" on known regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse nucleic acid sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing nucleic acid libraries can be implemented in much the same mariner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously. Still other spotting methods are described in PCT/US99/00730.

Pin-Based Methods

Another method which is useful for the preparation of nucleic acid arrays and libraries involves "pin based synthesis." This method is described in detail in U.S. Pat. No. 5,288,514. The method utilizes a substrate having a plurality of pins or other extensions. The pins are each inserted simultaneously into individual reagent containers in a tray. In a cormmon embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of nucleic acids, for example, the spacer may be selected from a wide variety of molecules which can be used in organic environments associated with synthesis as well as aqueous environments associated with binding studies. Examples of suitable spacers are polyethyleneglycols, dicarboxylic acids, polyarnines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., SOLID PHASE PEPTIDE SYNTHESIS, IRL Press (1989). In some embodiments, the spacer may provide for a cleavable function by way of, for example, exposure to acid or base.

Libraries on Multiple Substrates

Bead Based Methods

Yet another method which is useful for synthesis of nucleic acid arrays involves "bead based synthesis." A general approach for bead based synthesis is described in PCT/US93/04145 (filed Apr. 28, 1993).

For the synthesis of nucleic acids on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i.e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the fust container are deprotected and exposed to a second monomer (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single typl of molecule on its surface. Thus, all of the possible molecules formed from the first portions A, B, C, and the second portions D, E, and F have been formed.

The beads are then recombined into one container and additional steps such as are conducted to complete the synthesis of the polymer molecules. In a preferred embodiment, the beads are tagged with an identifying tag which is unique to the particular nucleic acid or probe which is present on each bead. A complete description of identifier tags for use in synthetic libraries is provided in co-pending application Ser. No. 08/146,886 (filed Nov. 2, 1993).

Solid supports

Solid supports used in the present invention include any of a variety of fixed organizational support matrices. In some embodiments, the support is substantially planar. In some embodiments, the support may be physically separated into regions, for example, with trenches, grooves, wells and the like. Examples of supports include slides, beads and solid chips. Additionally, the solid supports may be, for example, biological, nonbiological, organic, inorganic, or a combination thereof, and may be in forms including particles, strands, gels, sheets, tubing, spheres, containers, capillaries, pads, slices, films, plates, and slides depending upon the intended use.

Supports having a surface to which arrays of nucleic acids are attached are also referred to herein as "biological chips". The support is preferably, silica or glass, and can have the thickness of a microscope slide or glass cover slip. Supports that are transparent to light are useful when the assay involves optical detection, as described, e.g., in U.S. Pat. No. 5,545,531. Other useful supports include Langmuir Blodgett film, germanium, (poly)tetrafluorethylene, polystyrene, (poly)vinylidenedifluoride, polycarbonate, gallium arsenide, gallium phosphide, silicon oxide, silicon nitride, and combinations thereof. In one embodiment, the support is a flat glass or single crystal silica surface with relief features less than about 10 Angstoms.

The surfaces on the solid supports will usually, but not always, be composed of the same material as the substrate. Thus, the surface may comprise any number of materials, including polymers, plastics, resins, polysaccharides, silica or silica based materials, carbon, metals, inorganic glasses, membranes; or any of the above-listed substrate materials. Preferably, the surface will contain reactive groups, such as carboxyl, amino, and hydroxyl. In one embodiment, the surface is optically transparent and will have surface Si-OH functionalities such as are found on silica surfaces. In other embodiments, the surface will be coated with functionalized silicon compounds (see, for example, U.S. Pat. No. 5,919, 523).

Surface Density

The nucleic acid arrays described herein can have any number of nucleic acid sequences selected for different applications. Typically, there may be, for example, about 100 or more, or in some embodiments, more than 10 or 108. In one embodiment, the surface comprises at least 100 probe nucleic acids each preferably having a different sequence, each probe contained in an area of less than about 0.1 cm$^2$, or, for example, between about 1/mm$^2$ and 10,000/mm$^2$, and each probe nucleic acid having a defined sequence and location on the surface. In one embodiment, at least 1,000 different nucleic acids are provided on the surface, wherein each nucleic acid is contained within an area less than about $10^{-3}$ cm$^2$, as described, for example, in U.S. Pat. No. 5,510,270.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different nucleic acids is greater than about 60 different nucleic acids per 1 cm$^2$.

Arrays of nucleic acids irnmobilized on a surface which may be used also are described in detail in U.S. Pat. No. 5,744,305, the disclosure of which is incorporated herein. As disclosed therein, on a substrate, nucleic acids with different sequences are immobilized each in a lnown area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a known region of a substrate, having a surface area, for example, of about 1 cm$^2$ to $10^{-10}$ cm$^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{10}$ cm$^2$. For example, in one embodiment, there is provided a planar, non-porous support having at least a first surface, and a plurality of different nucleic acids attached to the first surface at a density exceeding about 400 different nucleic acidslcm$^2$, wherein each of the different nucleic acids is attached to the surface of the solid support in a different known region, has a different determinable sequence, and is, for example, at least 4 nucleotides in length. The nucleic acids may be, for example, about 4 to 20 nucleotides in length. The number of different nucleic acids may be, for example, 1000 or more. In the embodiment where polynucleotides of a known chemical sequence are synthesized at known locations on a substrate, and binding of a complementary nucleotide is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270.

Applications Using Nucleic Acid Arrays

The methods and compositions described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis, diabetes, and acquired diseases such as cancer, as disclosed in U.S. patent application Ser. No. 08/143,312. Genetic mutations may be detected by sequencing by hybridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. patent application Ser. No. 08/797,812, filed Feb. 7, 1997, and U.S. application Ser. No. 08/629,031, filed Apr. 8, 1996. Still other applications are described in U.S. Pat. No. 5,800,992.

Gene expression may be monitored by hybridization of large numbers of mRNAs in parallel using high density arrays of nucleic acids in cells, such as in microorganisms such as yeast, as described in Lockhart et al., Nature Biotechnology, 14:1675–1680 (1996). Bacterial transcript imaging by hybridization of total RNA to nucleic acid arrays may be conducted as described in Saizieu et al., Nature Biotechnology, 16:45–48 (1998). Accessing genetic information using high density DNA arrays is further described in Chee, Science 274:610–614 (1996).

Still other methods for screening target molecules for specific binding to arrays of polymers, such as nucleic acids, immobilized on a solid substrate, are disclosed, for example, in U.S. Pat. No. 5,510,270. The fabrication of arrays of polymers, such as nucleic acids, on a solid substrate, and methods of use of the arrays in different assays, are also described in: U.S. Pat. Nos. 5,677,195, 5,624,711, 5,599,695, 5,445,934, 5,451,683, 5,424,186, 5,412,087, 5,405,783, 5,384,261, 5,252,743 and 5,143,854; PCT WO 92/10092; and U.S. application Ser. No. 08/388,321, filed Feb. 14, 1995.

Devices for concurrently processing multiple biological chip assays are useful for each of the applications described above (see, for example, U.S. Pat. No. 5,545,531). Methods and systeins for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832. These methods permit a highly sensitive and resolved image to be obtained at high speed. Methods and apparatus for detection of fluorescently labeled materials are further described in U.S. Pat. Nos. 5,631,734 and 5,324,633.

Preferred Embodiments

In view of the technologies provided above, the present invention provides in one preferred embodiment, a method of preparing a nucleic acid array on a support, wherein each nucleic acid occupies a separate known region of the support and the nucleic acids are synthesized using the steps:

(a) activating a region of the support;

(b) attaching a nucleotide to a first region, the nucleotide having a masked reactive site linked to a protecting group;

(c) repeating steps (a) and (b) on other regions of the support whereby each of the other regions has bound thereto another nucleotide comprising a masked reactive site link to a protecting group, wherein the another nucleotide may be the same or different from that used in step (b);

(d) removing the protecting group from one of the nucleotides bound to one of the regions of the support to provide a region bearing a nucleotide having an unmasked reactive site;

(e) binding an additional nucleotide to the nucleotide with an unmasked reactive site;

(f) repeating steps (d) and (e) on regions of the support until a desired pluarlity of nucleic acids is synthesized, each nucleic acid occupying separate known regions of the support;

wherein the attaching steps farther include oxidizing the initially formed phosphite ester linkage to a phosphate ester linkage with a solution of about 0.005 M to about 0.05 M iodine in a mixture of water and organic solvent or solvents.

Preferably, the "activating" of step (a) is carried out using a channel block or photolithography technique, more preferably a photolithography technique. The "attaching" of step (b) is typically carried out using chemical means to provide a covalent bond between the nucleotide and a surface functional group present in the first region. In some embodiments, the surface functional group will be a group present on a nucleotide or nucleic acid that is already attached to the solid support. For example, nucleic acid arrays can be prepared using a solid support having a surface coated with poly-A nucleic acids to provide suitable spacing between the surface of the support and the nucleic acids that will be used in subsequent hybridization assays. Accordingly, the "attaching" can be, for example, by formation of a covalent bond between surface Si-OH groups and a group present on the first nucleotide of a nascent nucleic acid chain, or by formation of a covalent bond between groups present in a support-bound nucleic acid and a group present on the first nucleotide of a nascent nucleic acid. Typically, the groups present on nucleic acids which are used in covalent bond formation are the 3'- or 5-hydroxyl groups in the sugar portion or the molecule, or phosphate groups attached thereto.

The nucleotidcs used in this and other aspects of the present invention will typically be the naturally-occuring nucleotides, derived from, for example, adenosine, guanosine, uridine, cytidine and thymidine. In certain embodiments, however, nucleotide analogs or derivatives will be used (e.g., those nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer). The nucleotides will typically have a protecting group which is linked to, and masks, a reactive group on the nucleotide. A variety of protecting groups are useful in the invention and can be selected depending on the synthesis techniques employed. For example, channel block methods can use acid- or base-cleavable protecting groups to mask a hydroxyl group in a nucleotide. After the nucleotide is attached to the support or growing nucleic acid, the protecting group can be removed by flowing an acid or base solution through an appropriate channel on the support.

Similarly, photolithography techniques can use photoremoveable protecting groups. Some classes of photoremovable protecting groups include 6-nitroveratryl (NV), 6-nitropiperonyl (NP), methyl-6-nitroveratryl (MeNV), methyl-6-nitropiperonyl (MeNP), and 1-pyrenylmethyl (PyR), which are used for protecting the carboxyl terminus of an amino acid or the hydroxyl group of a nucleotide, for example. 6-nitroveratryloxycarbonyl (NVOC), 6-nitropiperonyloxycarbonyl (NPOC), methyl-6-nitroveratryloxycarbonyl (MeNVOC), methyl-6-nitropiperonyloxycarbonyl (MeNPOC), 1-pyrenylmethyloxycarbonyl (PyROC), which are used to protect the amino terminus of an amino acid are also preferred. Clearly, many photosensitive protecting groups are suitable for use in the present invention (see, U.S. Pat. No. 5,489,678 and PCT WO 94/10128).

In addition, novel photoremovable protecting groups such as 5'-O-pyrenylmethyloxy carbonyl (PYMOC) and methy-lnitropiperonyloxycarbonyl (MeNPOC) have been described in the copending U.S. patent application Ser. No. 08/630,148, filed Apr. 10, 1996, the contents of which are hereby incorporated by reference.

In addition to the above-described protecting groups, the present invention employs protecting groups, such as the 5'-X-2'-deoxythyrnidine 2-cyanoethyl 3'-N,N-diisopropylphosphoramidites in various solvents. In these protecting groups, X may represent the following photo-labile groups: ((a-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC).

Various methods for generating protected monomers have been described by the U.S. Pat. No. 5,744,305, which is incorporated by reference. Detailed methods for using photoremovable protecting groups are described in the U.S. Pat. No. 5,424,186, which is also hereby incorporated by reference.

The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed faster than their unsubstituted parent compounds, NVOC and NPOC, respectively.

In addition to the above-described references, photoclcavable protecting groups and methods of using such photocleavable protecting groups for polymer synthesis have been described in the copending application Ser. Nos. 08/630,148 (filed Apr. 10, 1996) and 08/812,005 (filed Mar. 5, 1997) which are incorporated by reference herein.

Step (c) provides that steps (a) and (b) can be repeated to attach nucleotides to other regions of the solid support.

One of skill in the art will appreciate that steps (a) and (b) can be repeated a number of times to produce a solid support having a layer of attached nucleotides. Preferably, each attached nucleotide is in a known position.

In subsequent steps (d), (e) and (f), the protecting group is removed from one of the nucleotides to reveal a reactive site on the nucleotide. Thereafter, an additional nucleotide (optionally having a masked reactive site attached to a protecting group) is attached to the support-bound nucleotide. As above, these steps can be repeated to selectively attach or bind an additional nucleotide to any of the support-bound nucleotides. Still further, the steps of deprotecting and attaching an additional nucleotide can be carried out on the newly added nucleotides to continue the synthesis of the nascent nucleic acid.

As noted above, the above steps are preferably carried out in combination with an oxidation step used to convert the initially formed phosphite ester linkage to a phosphate ester linkage. Earlier methods of oxidation used 0.1 M solutions of iodine. The present invention derives from the surprising discovery that significantly lower amounts of iodine (solutions from about 0.005 to about 0.05 M) can be used to accomplish the desired oxidation, yet provide arrays with improved sensitivity and functional performance. More preferably, the oxidation uses 0.02 M iodine in a mixture of water, pyridine and tetrahydrofuran (THF).

The oxidation mixture typically includes water and one or more organic solvents. Suitable solvents include aprotic solvents (e.g., tetrahydrofuran, pyridinc and lutidine or other weak bases). Preferably, the oxidation mixture includes water, pyridine and tetrahydrofaran. More preferably, the oxidation mixture includes water (about 5 to about 30%), pyridine (about 5 to about 30%) with the remainder being THF in addition to iodine in an amount sufficient to produce a concentration of from about 0.005 to about 0.05 M. In the most preferred embodiments, the oxidation mixture is 0.02 M iodine in a mixture of about 10% water, 20% pyridine and the remainder being THF.

In a further preferred embodiment, the preparing comprises:

a) removing a photorcmoveable protecting group from at least a first area of a surface of a substrate, the substrate comprising immobilized nucleotides on the surface, and the nucleotides capped with a photoremovable protective group, without removing a photoTemoveable protecting group from at least a second area of the surface;

b) simultaneously contacting the first area and the second area of the surface with a first nucleotide to couple the first nucleotide to the immobilized nucleotides in the first area, and not in the second area, the first nucleotide capped with a photoremovable protective group;

c) removing a photoremoveable protecting group from at least a part of the first area of the surface and at least a part of the second area;

d) simultaneously contacting the first area and the second area of the surface with a second nucleotide to couple the second nucleotide to the immobilized nucleotides in at least a part of the first area and at least a part of the second area;

e) performing additional removing and nucleotide contacting and coupling steps so that a matrix array of at least 100 nucleic acids having different sequences is formed on the support;

with the proviso that the phosphoramidite contaminant is present in an amount of 0.5 mole % or less.

In this embodiment of the invention, the steps of removing photoremoveable protecting groups, coupling nucleotides to specific areas, removing protecting groups from the coupled nucleotides, and coupling additional nucleotides can all be carried out as described in, for example, U.S. Pat. No. 5,510,270, with the added feature that the coupling steps are followed wvith oxidizing steps to convert phosphite ester linkages to phosphate ester linkages. The oxidizing steps use iodine mixtures as described above.

In still further preferred embodiments, the nucleoside phosphoramidite monomers used in the methods described above have the formula:

wherein B represents adenine, guanine, thymine, cytosine, uracil or analogs thereof; R is hydrogen, hydroxy, protected hydroxy, halogen or alkoxy; P is a phosphoramidite group; and PG is a photoremoveable protected group.

In the group of emodiments using monomers of formula (I), B is −10 preferably adenine, guanine, thymine, cytosine or uracil. More preferably, B is adenine, guanine, thymine, or cytosine, and R is hydrogen. Still more preferably, the array prepared using the monomers above comprises at least 10 different nucleid acids, more preferably at least 100 different nucleic acids, still more preferably at least 1000 different nucleic acids. Most preferably, the array comprises at least 10,000 to 100,000 or more different nucleic acids. Additionally, each different nucleic acid is in a region having an area of less than about 1 cm$^2$, more preferably less than about 1 mm$^2$.

In still other preferred embodiments, 13 is adenine, guanine, thymine, or cytosine; R is hydrogen; and the oxidation solution used is about 0.02 M iodine in a mixture of water, pyridine and THF.

In further preferred embodiments, B is adenine, guanine, thymine, or cytosine; R is hydrogen; PG is MeNPOC and the oxidation solution used is about 0.02 M iodine in a mixture of water, pyridine and THF.

In still further preferred embodiments, B is adenine, guanine, thymine, or cytosine; R is hydrogen; PG is MeNPOC, P is -P(OCH$_2$CH$_2$CN)N(iPr)$_2$ and the oxidation solution used is about 0.02 M iodine in a mixture of water, pyridine and THF.

One of skill in the art will appreciate that the present invention can be readily modified to use protected nucleoside phosphoramidite monomers wherein the protecting group on the 5' hydroxy is acid or base removeable. Such modifications will render the invention applicable to other synthesis methodologies such as flow channel and spotting methods described in more detail above. Regardless of the array synthesis methods, oxidation of the phosphite triester linkage to a phosphate triester linkage using dilute solutions of iodine, typically from about 0.005 M iodine to about 0.05 M iodine can dramatically increase the yield of nucleic acid synthesis on the substrate and lead to enhanced functional performance of the array.

EXAMPLES

In each of the examples below, the nucleic acid probe arrays were prepared using photolithography and a silica wafer as the solid substrate. Preparation is typically on a 5 inch by 5 inch wafer which can be cut into 49 replicates of a probe array having about 400,000 distinct probe sequences, or 400 replicates of a probe array having about 50,000 distinct probe sequences. The density of the nucleic acid probes is about 1–10 picomoles per cm$^2$.

Example 1

This example illustrates the enhanced sensitivity and functional performance that was achieved using arrays prepared with an oxidizing solution of 0.02 M iodine in tetrahydrofuran/pyridine/water (LowOx) in place of 0.1 MI solutions of iodine in the same solvent mixtures (70% tetrahydrofuran/20% pyridine/I 0% water) (Control).

HuGeneFl arrays (human gene expression full-length product arrays, catalog #510137 Affymetrix) were prepared using photolithography, but using either a 0.02 M or a 0.1 M iodine solution for the phosphite triester oxidation steps. The array were prepared in 49 replicates.

To evaluate the enhanced sensitivity of the arrays, replicates prepared from each method and taken from different portions of the wafer (e.g., top and/or bottom) were treated with a labeled target (human kidney total RNA, from Clonetech, #64030-1) spiked with additional amounts of known probes.

Table 1 summarizes the results of this evaluation. The data are wafer averaged. Background was measured according to standard methods and calculated as follows:

$$Q = \frac{1}{N} \sum_{i \in all\ bg\ cells} \frac{stdev_i}{\sqrt{pixel_i}} * SF * NF$$

$$Disc = \sum \frac{PM - MM}{PM + MM}$$

(for all probe pairs)

% P is the percent of probe sets called present;

% I,1.5 pM is the percent of 1.5 pM spikes detected as an increase in a comparison analysis (N=9) with fold change >2SDT;

% I@3 pM is the percent of 3 pM spikes detected as an increase in a comparison analysis (N=15) with fold change >2SDT;

% FC is the percent of probe sets detected incorrectly as an increase or decrease with fold change >2SDT;

NF is a normalization factor (a measure of signal similarity between the 2 arrays)

TABLE 1

| Array | Process | % P | % I @ 1.5 pM | % I @ 3 pM | Bkgd |
|-------|---------|-----|--------------|------------|------|
| A | LowOx | 42% | 61% | 93% | 475 |
| B | " | 38% | 56% | 88% | 612 |
| C | " | 37% | 51% | 88% | 551 |
| D | " | 29% | 17% | 67% | 911 |
| E | Control | 27% | 44% | 67% | 498 |
| F | " | 26% | 33% | 73% | 460 |
| G | " | 9% | 6% | 13% | 696 |

Array D exhibited a significantly increased background signal and consequently could not be used for comparison to other probe arrays. Of the remaining arrays (A–C with Low Ox; and E–G with Control oxidant), consistently improved signal levels were achieved with Arrays A–C.

Figure 1:
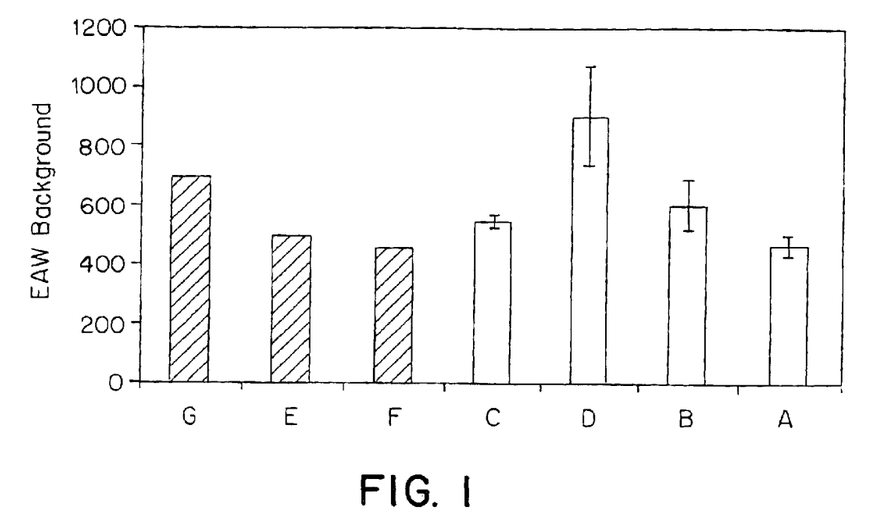
FIG. 1 is a bar graph which illustrates the background performance of each of the arrays. In this graph, the first three bars are for control (0.1 M iodine solutions) and the last four bars are for arrays constructed using a 0.02 M iodine oxidant solution. The background is comparable for all arrays with the exception of array D which exhibited a larger than expected background signal.

FIG. 1 is a bar graph which illustrates the background performance of each of the arrays. In this graph, the first three bars are for control (0.1 M iodine solutions) and the last four bars are for arrays constructed using a 0.02 M iodine oxidant solution. The background is comparable for all arrays with the exception of array D which exhibited a larger than expected background signal.

Figure 2:
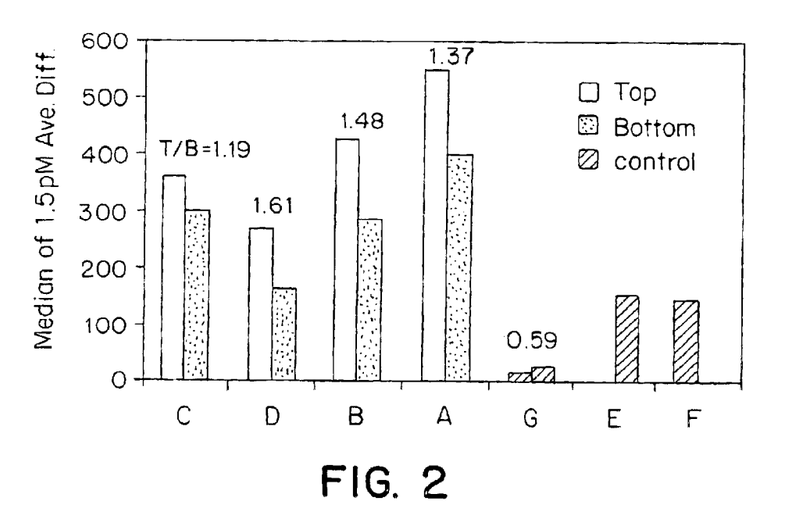
FIG. 2 is a bar graph which illustrates the enhanced functional performance of arrays A–D (LowOx) versus arrays E–G (Control) and compares arrays taken from the top or the bottom of the wafer (held in a vertical positions during assembly). The bars indicate the amount detection of 1.5 pM spike probes.

FIG. 2 is a bar graph which illustrates the enhanced functional performance of arrays A–D (LowOx) versus arrays E–G (Control) and compares arrays taken from the top or the bottom of the wafer (held in a vertical positions during assembly). The bars indicate the amount detection of 1.5 pM spike probes.

Figure 3:
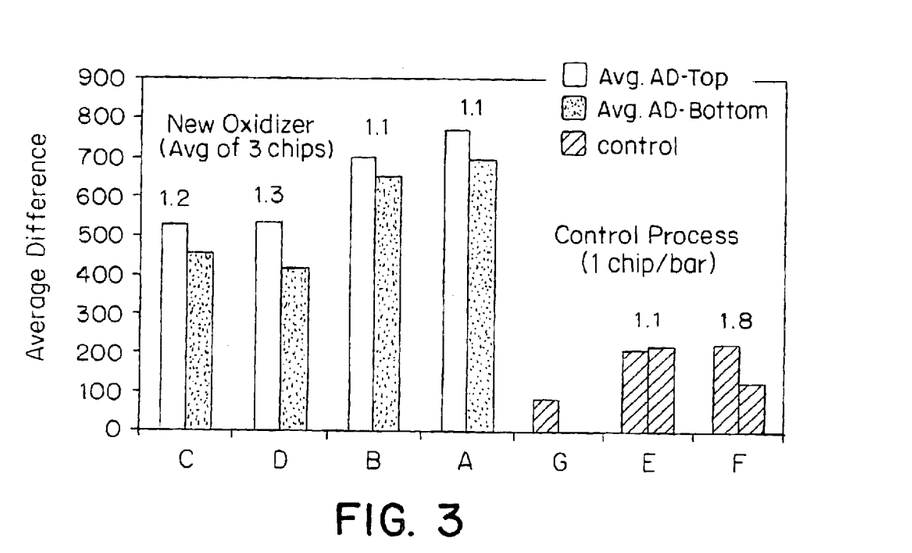
FIG. 3 illustrates the enhanced functional performance of arrays A–D (LowOx) versus arrays E–G (Control) measured by overall signal. As indicated in the figure, each of the LowOx arrays provided a substantially increased signal relative to the control arrays.

FIG. 3 illustrates the enhanced functional performance of arrays A–D (LowOx) versus arrays E–G (Control) measured by overall signal. As indicated in the figure, each of the LowOx arrays provided a substantially increased signal relative to the control arrays.

In summary, the table and figures indicate that the lower iodine oxidant formulation produces arrays with significantly improved functional performance as measured by signal, background and detection.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of oxidizing a phosphite ester linkage in a nucleic acid array to a phosphate linkage, comprising contacting said phosphite ester linkage with a solution of from 0.005M to 0.05 M in a mixture of water and organic solvent to form said phosphate linkage.

2. A method of synthesizing a nucleic acid array on a support, wherein each nucleic acid occupies a separate known region of the support, said synthesizing comprising:
 (a) activating a region of the support;
 (b) attaching a nucleotide to a first region, said nucleotide-having a masked reactive site linked to a protecting group;
 (c) repeating steps (a) and (b) on other regions of said support whereby each of said other regions has bound thereto another nucleotide comprising a masked reactive site link to a protecting group, wherein said another nucleotide may be the same or different from that used in step (b);
 (d) removing the protecting group from one of the nucleotides bound to one of the regions of the support to provide a region beaming a nucleotide having an unmasked reactive site;
 (e) binding an additional nucleotide to the nucleotide with an unmasked reactive site,
 (f) repeating step (d) and (c) on regions of the support until a desired plurality of nucleic acids is synthesized, each nucleic acid occupying separate known regions of the support;
 wherein said attaching and said binding are each made by covalently forming a phosphite triester linkage between said nucleotides and said unmasked reactive site and further comprising oxidizing said phosphite triester linkage to a phosphate trisect linkage, with a solution of from 0.005 M to 0.05 M in an aqueous solvent mixture.

3. A method in accordance with claim 2, wherein said synthesizing comprises the sequential steps of:
 (a) removing a photoremoveable protecting group from at least a first area of a surface of a substrate, said surface comprising immobilized nucleotides on said surface, said nucleotides capped with a photoremoveable protecting group, without removing a photoremoveable protecting group from at least a second area of said surface;
 (b) simultaneously contacting said first area and said second area of said surface with a first nucleotide to couple said first nucleotide to said immobilized nucleotides in said first area, and not in said second area, said first nucleotide capped with said photoremoveable protecting group;
 (c) removing a photoremoveable protecting group from at least a part of said first area of said surface and at least a pail of said second area;
 (d) simultaneously contacting said first area and said second area of said surface with a second nucleotide to couple said second nucleotide to said immobilized nucleotides in at least a part of said first area and at least a part of said second area;
 (e) performing additional removing and nucleotide contacting and coupling steps so that a matrix array of at least 100 nucleic acids having different sequences is formed on said support;
 with the proviso that the coupling steps further comprise oxidizing an initially formed phosphite ester linkage to a phosphite ester linkage using from 0.005 M to 0.05 M in an aqueous solvent mixture.

4. A method in accordance with claim 3, wherein said aqueous solvent mixture comprises iodine in an amount of 0.02 M.

5. A method in accordance with claim 3, wherein said nucleotides have the formula:

wherein
 B is a member selected from the group consisting of natural or unnatural adenine, natural or unnatural guanine, natural or unnatural thymine, natural or unnatural cytosine, and natural or unnatural uracil;
 R is a member selected from the group consisting of hydrogen, hydroxy, protected hydroxy, halogen and alkoxy, and
 PG is a photoremoveable protecting group.

6. A method in accordance with Claim S, wherein B is selected from the group consisting of adenine, guanine, cytosine and thymine and R is hydrogen.

7. A method in accordance with claim 5, wherein said array comprises at least 10 different nucleic acids.

8. A method in accordance with claim 5, wherein said array comprises at least 100 different nucleic acids.

9. A method in accordance with claim 5, wherein said array comprises at least 1000 different nucleic acids.

10. A method in accordance with claim 5, wherein said array comprises at least 10,000 different nucleic acids.

11. A method in accordance with claim 5, wherein said array comprises at least 100,000 different nucleic acids.

12. A method in accordance with claim 5, wherein each different nucleic acid is in a region having an area of less than about 1 cm$^2$.

13. A method in accordance with Claim 5, wherein each different nucleic acid is in a region having an area of less than about 1 mm$^2$.

14. A method in accordance with Claim 5, wherein said solution is 0.02 M iodine in a mixture of water, pyridine and THF.

15. A method in accordance with claim 5, wherein B is selected from the group consisting of adenine, guanine, cytosine and thymine, R is hydrogen, and said solution is 0.02 M iodine in a mixture of water, pyridine and THF.

16. A method in accordance with claim 5, wherein B is selected from the group consisting of adenine, guanine, cytosine and thymine, R is hydrogen, PG is McNPOC and said solution is 0.2 M iodine in a mixture of water, pyridine and THF.

17. A method in accordance with Claim 5, wherein B is selected from the group consisting of adenine, guanine, cytosine and thymine, R is hydrogen, PG is McNPOC, the phosphoramidite group is -P(OCH$_2$CH$_2$CN)N(iPr)$_2$ and said solution is 0.02 M iodine in a mixture of water, pyridine and THF.

18. The method of claim 5, wherein from 0.02 M to 0.05 M iodine is present in the aqueous solvent mixture.

* * * * *

UNITED STATES PATENT AND TRADEMARK OFFICE
CERTIFICATE OF CORRECTION

PATENT NO. : 6,833,450 B1
DATED : December 21, 2004
INVENTOR(S) : McGall et al.

It is certified that error appears in the above-identified patent and that said Letters Patent is hereby corrected as shown below:

Column 17,
Line 7, after "0.05M" insert -- iodine --;
Line 7, after "and" insert -- aprotic --;
Line 24, "beaming" should be -- bearing --;
Line 28, "(c)" should be -- (e) --;
Line 36, "trisect" should be -- triester --;
Line 37, after "0.05M" insert -- iodine --;
Line 55, "pail" should be -- part --;

Column 18,
Line 1, after "0.05M" insert -- iodine --;
Line 26, "Claim S" should be -- Claim 5 --;
Line 54, "McNPOC" should be -- MeNPOC --;
Line 55, "0.2M" should be -- 0.02M --;
Line 59, "McNPOC" should be -- MeNPOC --;

Signed and Sealed this

Nineteenth Day of July, 2005

JON W. DUDAS
*Director of the United States Patent and Trademark Office*